United States Patent [19]

Kawaguchi

[11] Patent Number: 4,975,371

[45] Date of Patent: Dec. 4, 1990

[54] HIGH VISCOUS SUBSTANCE BS-1 AND PROCESS FOR PRODUCING THE SAME

[75] Inventor: Katsumi Kawaguchi, Ichikawa, Japan

[73] Assignee: Kureha Kagaku Kogyo Kabushiki Kaisha, Tokyo, Japan

[21] Appl. No.: 54,264

[22] Filed: May 26, 1987

[30] Foreign Application Priority Data

May 30, 1986 [JP] Japan .................. 61-125347

[51] Int. Cl.$^5$ .................. C12P 19/04; C12N 1/20; C08B 37/00
[52] U.S. Cl. .................. 435/101; 435/83; 435/252.1; 435/852; 536/114; 536/123
[58] Field of Search .................. 435/83, 101, 852, 822, 435/252.1; 536/114, 123

[56] References Cited

U.S. PATENT DOCUMENTS 4,311,795 1/1982 Kang et al. .................. 435/852

FOREIGN PATENT DOCUMENTS 0001895 5/1979 European Pat. Off. .................. 435/852
0184755 6/1986 European Pat. Off. .
2168365 6/1986 United Kingdom .

Primary Examiner—Ronald W. Griffin
Assistant Examiner—Pamela S. Webber
Attorney, Agent, or Firm—John P. White

[57] ABSTRACT

Disclosed herein is a high viscous substance composition and its purified high viscous substance which are produced by cultivating a microbe belonging to genus *Klebsiella* and which are useful as an additive such as a thickening agent and/or an emulsion stabilizer for food, medicine, etc., and a process for producing such a high viscous substance composition and its purified high viscous substance.

16 Claims, 2 Drawing Sheets

HIGH VISCOUS SUBSTANCE BS-1 AND PROCESS FOR PRODUCING THE SAME

BACKGROUND OF THE INVENTION

The present invention relates to a high viscous substance composition and its purified high viscous substance which are produced by cultivating a microbe belonging to genus Klebsiella and which are useful as an additive such as a thickening agent and/or an emulsion stabilizer for food, medicine, etc., and a process for producing such a high viscous substance composition and its purified high viscous substance.

The aforementioned high viscous substance will be referred to as "a high viscous substance BS-1" hereinunder.

As high viscous substances which are produced by a microbe, polysaccharides such as xanthan gum which is produced by *Xanthomonas campestris,* dextran which is produced by *Leuconostoc mesenteroides* and pullulan which is produced by *Aureobasidium pullulans* are well known. On the other hand, carrageenan, tragacanth gum, etc. are known as high viscous substances obtained from a plant. These substances are now in wide use in the fields of food and medicine as a food additive such as a thickening agent, a dispersant and a modifier and, further, as a plasma substitute.

These substances have, however, disadvantages in that a comparatively high concentration must be added to obtain the intended effect and in that they are poor in long-term stability. Therefore, development of a high viscous substance which exhibits a high viscosity even in a low concentration and has excellent stability has been in demand in various fields including the fields of food and medicine.

The present inventors cultivated and tested various kinds of microbes in order to obtain an excellent high viscous substance which is usable in a field of a wide range. As a result, it has been found that it is possible to produce an excellent high viscous substance composition and its purified high viscous substance which exhibit a high-viscosity even in a low concentration by cultivating a strain of *Klebsiella pneumoniae* which belongs to genus Klebsiella. The present invention has been achieved on the basis of this finding.

The first object of the present invention is to provide a novel high viscous substance BS-1 composition which is obtained by cultivating a microbe belonging to genus Klebsiella and which exhibits a high viscosity and good stability by the addition of a comparatively low concentration of the substance composition.

The second object of the present invention is to provide a novel high viscous substance BS-1 which is obtained by purifying the aforementioned high viscous substance BS-1 composition and which exhibits a high viscosity and good stability by the addition of a comparatively low concentration of the substance.

The third object of the present invention is to provide a process for producing the aforementioned high viscous substance BS-1 composition, comprising cultivating a microbe belonging to genus Klebsiella.

The fourth object of the present invention is to provide a process for producing the aforementioned high viscous substance BS-1, comprising purifying the aforementioned high viscous substance BS-1 composition.

The fifth object of the present invention is to provide a thickening agent and/or an emulsion stabilizer which contains the aforementioned high viscous substance BS-1 composition or the aforementioned high viscous substance BS-1 as an active ingredient.

The sixth object of the present invention is to provide a process for increasing the viscosity of food, medicine, cosmetic, chemicals or the like and/or stabilizing the emulsion thereof by adding the aforementioned high viscous substance BS-1 composition or the aforementioned high viscous substance BS-1 thereto.

SUMMARY OF THE INVENTION

In a first aspect of the present invention, there is provided a high viscous substance BS-1 composition which is produced by cultivating a microbe belonging to genus Klebsiella and which has the following properties:

(a) External appearance: tasteless and odorless white powder
(b) Solubility: readily soluble in water, scarcely soluble in methanol, ethyl acetate, chloroform and benzene, and hydrolyzable by mineral acids
(c) Viscosity : 2,000 to 3,000 centipoises (in 1 % aqueous solution at a temperature of 30° C. and a shear rate of 3.83 $sec^{-1}$)
(d) Composition of main constituent sugars: 50 to 70 % of galactose, 0.5 to 3 % of mannose, 1 to 5 % of glucose and 25 to 37 % of glucuronic acid
(e) Color reaction:
Phenol-sulfuric acid reaction: positive
Carbazole-sulfuric acid reaction: positive
Molisch reaction: positive
Ninhydrin reaction: positive or slightly positive In a second aspect of the present invention, there is provided a high viscous substance BS-1 which is obtained by purifying a high viscous substance composition produced by cultivating a microbe belonging to genus Klebsiella and which has the following properties:

(a) External appearance: tasteless and odorless white powder
(b) Solubility: readily soluble in water, scarcely soluble in methanol, ethyl acetate, chloroform and benzene, and hydrolyzable by mineral acids
(c) Viscosity : 2,400 to 2,600 centipoises (in 1 % aqueous solution at a temperature of 30° C. and a shear rate of 3.83 $sec^{-1}$)
(d) Composition of main constituent sugars: 60 to 65 % of galactose, 1.5 to 2.5 % of mannose, 2 to 3 % of glucose and 30 to 35 % of glucuronic acid
(e) Color reaction:
Phenol-sulfuric acid reaction: positive
Carbazole-sulfuric acid reaction: positive
Molisch reaction: positive
Ninhydrin reaction: negative
(f) Ultimate analysis value:
C: 37.5 to 39 %
H: 5.5 to 6 %
N: 0 to 0.2 %

In a third aspect of the present invention, there is provided a process for producing the high viscous substance BS-1 composition, comprising the steps of: cultivating a microbe belonging to genus Klebsiella which is productive of the high viscous substance BS-1; and separating and collecting the high viscous substance BS-1 composition from the culture.

In a fourth aspect of the present invention, there is provided a process for producing the high viscous substance BS-1, comprising the steps of: cultivating a microbe belonging to genus Klebsiella which is productive of the high viscous substance BS-1; separating and collecting the high viscous substance BS-1 composition from the culture; and carrying out at least one time of the operation of redeposition thereof by dissolving the high viscous substance BS-1 composition in water and adding an organic solvent which does not dissolve the high viscous substance BS-1, and/or treating the aqueous solution thereof by chromatography and/or dialysis.

In a fifth aspect of the present invention, there is provided the high viscous substance BS-1 composition produced by the above-mentioned process.

In a sixth aspect of the present invention, there is provided the high viscous substance BS-1 produced by the above-mentioned process.

In a seventh aspect of the present invention, there is provided a thickening agent and/or an emulsion stabilizer which contains the high viscous substance BS-1 composition as an active ingredient.

In an eighth aspect of the present invention, there is provided a thickening agent and/or an emulsion stabilizer which contains the high viscous substance BS-1 as an active ingredient.

In a ninth aspect of the present invention, there is provided a method of increasing the viscosity of food, medicine, cosmetic or chemicals and/or stabilizing the emulsion thereof by adding thereto the high viscous substance BS-1 composition.

In a tenth aspect of the present invention, there is provided a method of increasing the viscosity of food, medicine, cosmetic or chemicals and/or stabilizing the emulsion thereof by adding thereto the high viscous substance BS-1.

BRIEF DESCRIPTION OF THE DRAWINGS

In the accompanying drawings.

DETAILED DESCRIPTION OF THE INVENTION

Figure 1:
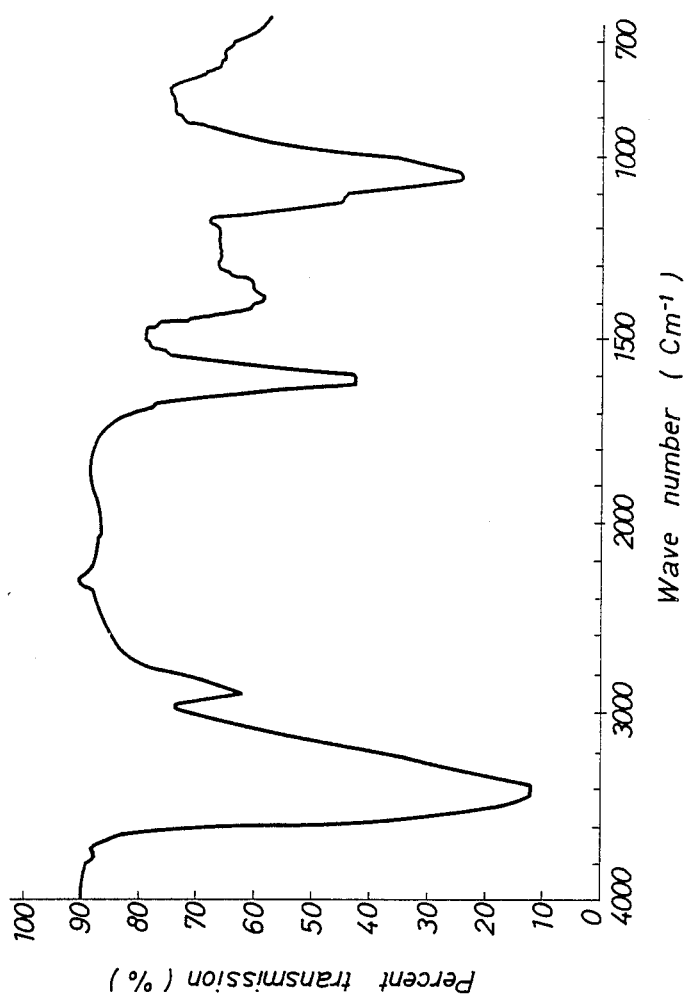
FIG. 1 shows an infrared absorption spectrum of a high viscous substance BS-1.

A high viscous substance BS-1 composition according to the present invention is a high viscous substance produced by cultivating a microbe belonging to genus Klebsiella. The substance BS-1 composition which is separated and collected from the culture of the microbe has the following properties. The "composition of the main constituent sugars" in the present invention shows the percentage of each of the main constituent sugars to total of the main constituent sugars contained in the high viscous substance BS-1 composition or the high viscous substance BS-1.

(a) External appearance: tasteless and odorless white powder
(b) Solubility: readily soluble in water, scarcely soluble in methanol, ethyl acetate, chloroform and benzene, and hydrolyzable by mineral acids
(c) Viscosity: 2,000 to 3,000 centipoises (in 1% aqueous solution at a temperature of 30° C. and a shear rate of 3.83 sec$^{-1}$)
(d) Composition of main constituent sugars: 50 to 70% of galactose, 0.5 to 3% of mannose, 1 to 5% of glucose and 25 to 37% of glucuronic acid
(e) Color reaction:
Phenol-sulfuric acid reaction: positive
Carbazole-sulfuric acid reaction: positive
Molisch reaction: positive
Ninhydrin reaction: positive or slightly positive A high viscous substance BS-1 according to the present invention which is obtained by purifying a high viscous substance composition produced by cultivating a microbe which belongs to genus Klebsiella, has the following properties:

(a) External appearance: tasteless and odorless white powder
(b) Solubility: readily soluble in water, scarcely soluble in methanol, ethyl acetate, chloroform and benzene, and hydrolyzable by mineral acids
(c) Viscosity: 2,400 to 2,600 centipoises (in 1% aqueous solution at a temperature of 30° C. and a shear rate of 3.83 sec$^{-1}$)
(d) Composition of main constituent sugars: 60 to 65% of galactose, 1.5 to 2.5% of mannose, 2 to 3% of glucose and 30 to 35% of glucuronic acid
(e) Color reaction:
Phenol-sulfuric acid reaction: positive
Carbazole-sulfuric acid reaction: positive
Molisch reaction: positive
Ninhydrin reaction: negative
(f) Ultimate analysis value:
C : 37.5 to 39%
H : 5.5 to 6%
N : 0 to 0.2%

A process for producing a high viscous substance BS-1 composition according to the present invention is characterized in that it comprises the steps of culturing a microbe which belongs to genus Klebsiella, and separating and collecting a high viscous substance BS-1 composition from the culture.

Any species and strain of microbes belonging to genus Klebsiella is unlimitedly usable in the present invention so long as it is productive of a high viscous substance BS-1. A strain of *Klebsiella pneumoniae* is preferably used in the present invention. Specifically, a strain of *Klebsiella pneumoniae* which is highly productive of a high viscous substance BS-1 has been separated from the water of the Sumida river in Japan and identified. From the results of examination of the microbiological properties thereof, it has been found that the above-described strain belongs to *Klebsiella pneumoniae* described in Bergey's Manual of Determinative Bacteriology (1974). Further, since the strain is negative in the MR test and positive in the VP test, this strain is surely assumed to be different from Friedländer's bacillus and to be *Klebsiella pneumoniae* in a broad sense. The microbiological properties of this strain of Klebsiella pneumoniae will be described in the following.

(1) Morphology: bacillus of a single cell having a capsule, no spore and a size of 0.7 to 0.9 × 1.0 to 2.0 μm
(2) Gram's stain: negative
(3) Observation on a culture medium of agar-agar: formation of a white colony having a circular or indefinite shape, and a slimy viscous substance
(4) Motility: negative
(5) Catalase: positive
(6) Oxidase : negative
(7) β-galactosidase: positive
(8) Generation of gases from glucose: positive
(9) Generation of acids from a carbohydrate: Generation of acids from arabinose, inositol, lactose, maltose, mannitol, sorbitol, sucrose, xylose, rhamnose, raffinose, trehalose and salicin: positive Generation of acids from adonitol: negative
(10) Utilization of citrate: positive
(11) Utilization of malonate: positive
(12) Utilization of gluconate: positive
(13) VP (Voges Proskauer) test: positive
(14) MR (methyl red) test: negative
(15) Reduction of nitrate: positive
(16) Hydrolysis of urea: positive
(17) Hydrolysis of arginine: negative
(18) Hydrolysis of gelatin: negative
(19) Phenylalanine test: negative
(20) Generation of indole: negative
(21) Generation of hydrogen sulfide from TSI agar-agar: negative
(22) Lysine decarboxylase: positive
(23) Ornithine decarboxylase: negative The strain having the above-described microbiological properties was deposited in Fermentation Research Institute, Agency of Industrial Science and Technology, Japan under the strain name of *Klebsiella pneumoniae* KPS 5002 and the deposit number of FERM P-625, and is preferably used in the present invention.

Among the microbes belonging to genus *Klebsiella*, *Klebsiella pneumoniae* is, as well known, readily mutated by radiation of ultraviolet rays, X-rays, radiant rays, etc., or by using a mutagen (e.g., nitrosoguanidine, nitrogen mustard and Acridine Orange ®) as the mutating means. Any mutant that is obtained in this way and is productive of a high viscous substance BS-1 is usable in the present invention as a strain of Klebsiella pneumoniae. Furthermore, a strain or a mutant thereof other than *Klebsiella pneumoniae* is also usable in the present invention so long as it belongs to genus Klebsiella and is productive of a high viscous substance BS-1.

A process for producing a high viscous substance BS-1 composition by utilizing a strain of *Klebsiella pneumoniae* will be explained in the following as an embodiment of the present invention.

A high viscous substance BS-1 composition according to the present invention is produced by subjecting the above-described strain to aerobic cultivation such as shake culture or stir culture with aeration in a solid or liquid culture medium which contains a carbon source, nitrogen source and other nutrients necessary for growing. The carbon source used in the medium is exemplified by sugars such as lactose, sucrose, maltose, galactose, glucose, fructose and the like.

Among these, lactose is preferable. The concentration of these sugars in the culture medium is not specified so long as it allows the microbe used to grow, but ordinarily it is 1 to 10% (w/v) and preferably 3 to 5% (w/v). The nitrogen source in the medium is exemplified by organic matters such as polypeptone, yeast extract, meat extract and TRIPTICASE ® (partially hydrolyzed casein produced by BBL MICROBIOLOGY SYSTEMS), and inorganic matters such as nitrate and ammonium salt, but an organic nitrogen source is preferable from the viewpoint of the productivity of the substance BS-1. Furthermore, it is possible to add a phosphate such as monopotassium phosphate or dipotassium phosphate, a trace amount of metals such as iron, copper, magnesium, manganese, molybdenum, zinc and boron, vitamins such as biotin, thiamine and vitamin $B_{12}$, and nucleic acids to the culture medium, if necessary.

The cultivating temperature in the medium is 20° to 37° C., which is the optimum temperature range for the proliferation of the microbe used, and is preferably 25° to 32° C. The pH of the culture medium is not specified, but is preferably 4 to 8, and more preferably in the vicinity of neutrality. The cultivation may be carried out until the viscosity of the medium reaches to its maximum, but actually, the cultivating time is preferably 3 to 7 days considering the productive efficiency.

When the above-described strain is cultivated under the above-described conditions, the viscosity of the culture medium is raised with the lapse of time and reaches 200 to 300 centipoises 5 days after. From this fact it is understood that a substance BS-1 has been produced and accumulated in the culture medium.

After the end of the cultivation, the substance BS-1 composition is separated and collected by an ordinary method. For example, when a liquid medium is used, the culture liquid is diluted with water after the end of the cultivation, impurities such as germs are removed by centrifugal separation or the like, and thereafter an organic solvent such as ethyl alcohol, methyl alcohol, isopropyl slcohol and acetone or a quaternary amine such as cetyl trimethyl ammonium and butylamide is added thereto, thereby precipitating a crude substance BS-1. After the precipitate is washed with the organic solvent and dehydrated and defatted with acetone, it is dried to obtain a high viscous substance BS-1 composition.

The high viscous substance BS-1 composition obtained by this method has the following properties:
(a) External appearance: tasteless and odorless white powder
(b) Solubility: readily soluble in water, scarcely soluble in methanol, ethyl acetate, chloroform and benzene, and hydrolyzable by mineral acids
(c) Viscosity: 2,000 to 3,000 centipoises (in 1% aqueous solution at a temperature of 30° C. and a shear rate of 3.83 $sec^{-1}$)
(d) Composition of main constituent sugars: 50 to 70% of galactose, 0.5 to 3% of mannose, 1 to 5% of glucose and 25 to 37% of glucuronic acid
(e) Color reaction:
  Phenol-sulfuric acid reaction: positive
  Carbazole-sulfuric acid reaction: positive
  Molisch reaction: positive
  Ninhydrin reaction: positive or slightly positive In the present invention, it is possible to obtain a high viscous substance BS-1 by further purifying the thus obtained high viscous substance BS-1 composition according to the following methods:

The operation of redeposition thereof by dissolving the high viscous substance BS-1 composition in water and adding an organic solvent such as ethyl alcohol which does not dissolve the high viscous substance BS-1 is carried out at least one time, and/or the aqueous solution thereof is treated by chromatography and/or dialysis. The high viscous substance BS-1 obtained by this method has the following properties:
(a) External appearance: tasteless and odorless white powder
(b) Solubility: readily soluble in water, scarcely soluble in methanol, ethyl acetate, chloroform and benzene, and hydrolyzable by mineral acids
(c) Viscosity: 2,400 to 2,600 centipoises (in 1% aqueous solution at a temperature of 30° C. and a shear rate of 3.83 $sec^{-1}$)
(d) Composition of main constituent sugars: 60 to 65% of galactose, 1.5 to 2.5% of mannose, 2 to 3% of glucose and 30 to 35% of glucuronic acid (e) Color reaction: Phenol-sulfuric acid reaction: positive Carbazole-sulfuric acid reaction: positive Molisch reaction: positive Ninhydrin reaction: negative (f) Ultimate analysis value:
C : 37.5 to 39%
H : 5.5 to 6%
N : 0 to 0.2%

The high viscous substance BS-1 composition obtained by the above-described method and the high viscous substance BS-1 obtained by purifying the high viscous substance BS-1 composition are readily dissolved in water to become a transparent solution showing non-Newtonian flow, and exhibits a high viscosity even in a low concentration. Therefore, they are applicable to wide uses in the fields of food, medicine, cosmetic and chemicals such as agricultural chemical and industrial chemicals as a thickening agent, an anti-dripping agent, a dispersant, a taste improver, a freeze stabilizer, a plasma substitute or the like.

Furthermore, since these substances also exhibit a high emulsion stability even in a low concentration, it is excellent as an emulsion stabilizer.

The present invention will be explained in more detail with reference to the following examples.

EXAMPLE 1

(1) Production of a high viscous substance BS-1 composition:

*Klebsiella pneumoniae* KPS5002 (DEPOSIT No. FERM P-625) which had been proliferated in a slant culture medium comprising 3 wt% lactose, 0.35 wt% TRIPTICASE® 0.6 wt% monopotassium phosphate, 0.07 wt% magnesium sulfate, and 1.4 wt% agar-agar was scraped up with a platinum loop, and inoculated into a 10 ml of a liquid culture medium which was the same in the composition as the above-described slant culture medium except that no agar-agar was contained, thereafter subjected to shake culture at 30° C. for one day as pre-culture.

The pre-culture was next inoculated, under a sterile atmosphere, into a 1( of a liquid culture medium which had the same composition as that of the medium used in the preculture and which had been sterilized for 15 minutes at 120° C., and subjected to shake culture at 120 rpm at 30° C. for 5 days. The culture liquid became viscous with the progress of the cultivation, whereby the production and accumulation of a substance BS-1 being observed therein.

The culture liquid obtained was subjected to centrifugal separation at 18,000 rpm for 15 minutes to remove germs therefrom, and the double amount of ethanol was added thereto to precipitate the substance BS-1 composition. The deposited crude substance BS-1 composition was entwined around a glass rod and after it was repeatedly washed with ethanol, acetone was added thereto to homogenize the substance BS-1 composition and acetone. Acetone was thereafter removed and the substance BS-1 composition was dried in a desiccator to obtain 9 g of the dried substance. The results of examination of the physical and chemical properties of the dried substance obtained will be shown in the following. From these results, the substance was identified as a high viscous substance BS-1 composition.

(a) External appearance: tasteless and odorless white powder (b) Solubility: readily soluble in water, scarcely soluble in methanol, ethyl acetate, chloroform and benzene, and hydrolyzable by mineral acids (c) Viscosity: 2,000 to 3,000 centipoises (in 1 % aqueous solution at a temperature of 30° C. and a shear rate of 3.83 sec$^{-1}$)

(d) Composition of main constituent sugars: 62.1 % of galactose, 1.5 % of mannose, 3.2 % of glucose and 33.2 % of glucuronic acid (e) Color reaction:
Phenol-sulfuric acid reaction: positive
Carbazole-sulfuric acid reaction: positive
Molisch reaction: positive
Ninhydrin reaction: ±

(2) Purification of the high-viscosity substance BS-1 composition:

9 g of the high viscous substance BS-1 composition obtained by the above-described method was dissolved in distilled water and insoluble substances were removed by centrifugal separation. The operation of redeposition of the high viscous substance BS-1 composition by dissolving the substance BS-1 composition in water and adding ethanol thereto was repeated two times, and deposited substance was dissolved in distilled water. The aqueous solution was dialyzed for 24 hours through a dialysis membrane against pure water, and was thereafter dried in a vacuum freeze drier to obtain 6 g of white purified bulk substance. The physical and chemical properties of the purified substance obtained are as follows. From those properties, the substance was identified as a high viscous substance BS-1.

(a) External appearance: tasteless and odorless white powder (b) Solubility: readily soluble in water, scarcely soluble in methanol, ethyl acetate, chloroform and benzene, and hydrolyzable by mineral acids (c) Viscosity: 2,400 to 2,600 centipoises (in 1 % aqueous solution at a temperature of 30° C. and a (d) Composition of main constituent sugars: 62.9 % of galactose, 1.8 % of mannose, 2.6 % of glucose and 32.6 % of glucuronic acid

[ Content of main constituent sugars in the specimen: 55.9% of galactose, 1.8% of mannose, 2.4% of glucose and 28.9% of glucuronic acid ]

(e) Color reaction:
Phenol-sulfuric acid reaction: positive
Carbazole-sulfuric acid reaction: positive
Molisch reaction: positive
Ninhydrin reaction: negative (f) Specific rotatory power: $[\alpha]_D^{27} = +127°$ (g) Ultimate analysis value:
C : 38.5 %
H : 5.8 %
N : 0.1 %

FIG. 1 shows the infrared absorption spectrum (KBr tablet method) of the high viscous substance BS-1 obtained by the above-described method.

In order to explain the usefulness of a high viscous substance BS-1 composition and a high viscous substance BS-1 according to the present invention, examples of using the substance BS-1 as a thickening agent and an emulsion stabilizer will now be shown in Example 2 and 3, respectively.

EXAMPLE 2

The high viscous substance BS-1 obtained in Example 1 was dissolved in water to prepare an aqueous solution containing 1 % of the substance. As comparative examples, aqueous solutions containing 1% of commercially available xanthan gum, carrageenan and tragacanth gum, respectively, were prepared. The viscosity of each of these aqueous solutions at 20° C. was measured.

Figure 2:
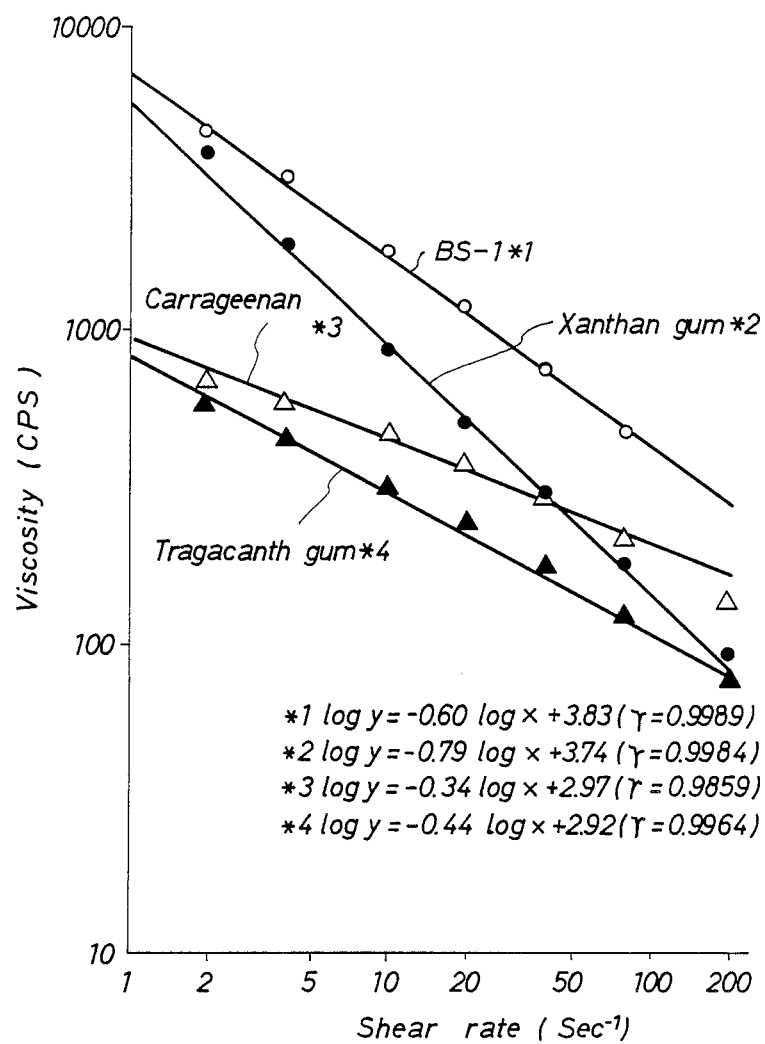
FIG. 2 shows the viscosity of the high viscous substance BS-1 as compared with those of commercially available thickening agents.

The results are shown in FIG. 2. As is clear from FIG. 2, the viscosity of the substance BS-1 took the highest value at any shear rate, and when the shear rate was 1 sec$^{-1}$, it reached about 7,000 centipoises.

In addition, since the aqueous solution of the substance BS-1 is colorless and transparent, it is advantageously usable as a thickening agent.

EXAMPLE 3

0.5 wt % (based on the total amount of an intended emulsion) of the substance BS-1 obtained in Example 1 was added to distilled water which had been heated to 60° to 70° C., and dissolved therein under stirring by a homogenizer. Respectively, 20 wt % and 40 wt % (based on the total amount of the intended emulsion) of soybean oils heated to the same temperature were added thereto and the mixtures were homogenized again to make emulsions having each the O/W ratios of 2/8 and 4/6. These emulsions were put into graduated test tubes and were left at room temperature. The stabilities of the emulsions were observed 1 day, 7 days and 1 month after.

As comparative examples, the same amounts of sucrose monostearate, Tween ® 80 and CMC (carboxymethylcellulose) were used to make the respective emulsions in the same procedures as the above. The stability of each of the emulsions was simultaneously observed. The results are shown in Table 1.

As is obvious from Table 1, the substance BS-1 exhibited the most excellent emulsion stability and the emulsions obtained by using the substance BS-1 showed a very smooth and creamy state, which state remained unchanged even one month after.

(d) Composition of main constituent sugars: 50 to 70 % of galactose, 0.5 to 3 % of mannose, 1 to 5 % of glucose and 25 to 37 % of glucuronic acid
(e) Color reaction:
Phenol-sulfuric acid reaction: positive
Carbazole-sulfuric acid reaction: positive
Molisch reaction: positive
Ninhydrin reaction: positive or slightly positive 2. A high viscous substance BS-1 which is obtained by purifying the high viscous substance BS-1 composition according to claim 1 which has the following properties:
(a) Appearance: tasteless and odorless white powder;
(b) Solubility: readily soluble in water, scarcely soluble in methanol, ethyl acetate, chloroform and benzene, and hydrolyzable by mineral acids;
(c) Viscosity: 2,400 to 2,600 centipoise (in 1% aqueous solution at a temperature of 30° C. and a shear rate of 3.83 second$^{-1}$;
(d) Composition of main constituent sugars: 60 to 65% of galactose, 1.5 to 2.5% of mannose, 2 to 3% of glucose and 30 to 35% of glucuronic acid;
(e) Color reaction:
phenol-sulfuric acid reaction—positive
carbazole-sulfuric acid reaction—positive
Molisch reaction—positive
ninhydrin reaction—negative; and
(f) Ultimate analysis value:
carbon:37.5 to 39%
hydrogen:5.5 to 6%
nitrogen:0 to 0.2%.

3. The high viscous substance BS-1 composition according to claim 1, wherein said microbe belonging to genus Klebsiella is a *Klebsiella pneumoniae* strain.

4. The high viscous substance BS-1 composition according to claim 3, wherein said strain is *Klebsiella pneumoniae* KPS 5002 (DEPOSIT No. FERM P-625) species.

TABLE 1

| | O/W ratio | | | | | |
|---|---|---|---|---|---|---|
| | 2/8 | | | 4/6 | | |
| | Elapsed Time | | | | | |
| Emulsifier | 1 day | 7 days | 1 month | 1 day | 7 days | 1 month |
| Substance BS-1 according to the present invention | + + | + + | + + | + + | + + | + + |
| Xanthan gum | + + | + + | ± | + + | + + | ± |
| Sucrose monostearate (HLB 15) | + + | — | — | ± | — | — |
| Tween ® 80 | + + | ± | — | + + | — | — |
| CMC | ± | — — | — — | — | — — | — — |

(note)
+ + complete emulsification, ± slight separation of layers, — separation of layers (formation of cloudy water layer), — — separation of layers (formation of transparent water layer)

What is claimed is:

1. A high viscous substance BS-1 composition which is produced by cultivating a microbe belonging to genus Klebsiella and which has the following properties:
(a) External appearance: tasteless and odorless white powder
(b) Solubility: readily soluble in water, scarcely soluble in methanol, ethyl acetate, chloroform and benzene, and hydrolyzable by mineral acids
(c) Viscosity: 2,000 to 3,000 centipoises (in 1 % aqueous solution at a temperature of 30° C. and a shear rate of 3.83 sec$^{-1}$)

5. A process for producing a high viscous substance BS-1 composition of claim 1, comprising the steps of: cultivating a microbe belonging to genus Klebsiella which is productive of said high viscous substance BS-1 composition; and separating and collecting said high viscous substance BS-1 composition from the culture.

6. A process for producing a high viscous BS-1 composition of claim 2, comprising the steps of: carrying out at least once the operation of redeposition thereof dissolving said high viscous substance BS-1 and/or treating the aqueous solution thereof by chromatography and/or dialysis.

7. The process according to claim 5, wherein said microbe is a *Klebsiella pneumoniae* strain.

8. The process according to claim 7, wherein said strain is *Klebsiella pneumoniae* KPS 5002 (DEPOSIT No. FERM P-625) species.

9. The process according to claim 7, wherein said Klebsiella pneumoniae strain is cultivated in a culture medium which contains lactose and organic nitrogen source and which has a pH of 4 to 8.

10. The process according to claim 9, wherein said cultivation is carried out at 25° to 32° C. for 3 to 7 days.

11. A high viscous substance BS-1 composition produced by the process of claim 5, having the following properties:
(a) Appearance; tasteless and odorless white powder;
(b) Solubility: readily soluble in water, scarcely soluble in methanol, ethyl acetate, chloroform and benzene, and hydrolyzable by mineral acids;
(c) Viscosity: 2,000 to 3,000 centipose (in 1% aqueous solution at a temperature of 30° C. and a shear rate of 3.83 second$^{-1}$;
(d) Composition of main constituent sugars: 50 to 70 % of galactose, 0.5 to 3% of mannose, 1 to 5% of glucose and 25 to 37% of glucuronic acid; and
(e) Color reaction:
phenol-sulfuric acid reaction—positive
carbazole-sulfuric acid reaction—positive
Molisch reaction—positive
ninhydrin reaction—positive or slightly positive.

12. A high viscous substance BS-1 produced by the process of claim 6, having the following properties:
(a) Appearance: tasteless and odorless white powder;
(b) Solubility: readily soluble in water, scarcely soluble in methanol, ethyl acetate, chloroform and benzene, and hydrolyzable by mineral acids;
(c) Viscosity: 2,400 to 2,600 centipoise (in 1% aqueous solution at a temperature of 30° C. and a shear rate of 3.83 second$^{-1}$.
(d) Composition of main constituent sugars: 60 to 65% of galactose, 1.5 to 2.5% of mannose, 2 to 3% of glucose and 30 to 30% of glucuronic acid;
(e) Color reaction:
phenol-sulfuric acid reaction—positive
carbazole-sulfuric acid reaction—positive
Molisch reaction—positive
ninhydrin reaction—negative; and
(f) Ultimate analysis value:
carbon:37.5 to 39%
hydrogen:5.5 to 6%
nitrogen:0 to 0.2%

13. A thickening agent and/or an emulsion stabilizer which contains a high viscous substance BS-1 composition according to claim 1 as an active ingredient.

14. A thickening agent and/or an emulsion stabilizer which contains a high viscous substance BS-1 according to claim 2 as an active ingredient.

15. A method of increasing the viscosity of food, medicine, cosmetic or chemicals and/or stabilizing the emulsion thereof by adding thereto a high viscous substance BS-1 composition according to claim 1.

16. A method of increasing the viscosity of food, medicine, cosmetic or chemicals and/or stabilizing the emulsion thereof by adding thereto a high viscous substance BS-1 according to claim 2.

* * * * *